(12) United States Patent
Casse et al.

(10) Patent No.: US 11,545,019 B2
(45) Date of Patent: *Jan. 3, 2023

(54) METHOD AND SYSTEM FOR PATIENT MANAGEMENT USING RULES ENGINE

(71) Applicant: Fisher & Paykel Healthcare Limited, Auckland (NZ)

(72) Inventors: Benjamin Wilson Casse, Auckland (NZ); Christopher Harding Campbell, Auckland (NZ); Katarzyna Sobolewska, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 17/651,652

(22) Filed: Feb. 18, 2022

(65) Prior Publication Data
US 2022/0172595 A1 Jun. 2, 2022

Related U.S. Application Data

(63) Continuation of application No. 16/481,047, filed as application No. PCT/IB2018/050472 on Jan. 26, 2018, now Pat. No. 11,288,942.
(Continued)

(51) Int. Cl.
*G08B 21/04* (2006.01)
*G16H 20/40* (2018.01)
(Continued)

(52) U.S. Cl.
CPC ........ *G08B 21/0453* (2013.01); *A61B 5/4818* (2013.01); *A61B 5/4833* (2013.01);
(Continued)

(58) Field of Classification Search
None
See application file for complete search history.

(56) References Cited

U.S. PATENT DOCUMENTS 11,288,942 B2 * 3/2022 Casse ................ A61M 16/0051
2005/0192845 A1 * 9/2005 Brinsfield .............. G16H 20/17
705/3

(Continued)

FOREIGN PATENT DOCUMENTS

WO WO 2014/196535 12/2014
WO WO 2015/025264 2/2015
(Continued)

OTHER PUBLICATIONS

International Search Report and Written Opinion for PCT/IB2018/050472 dated Apr. 27, 2018 in 11 pages.
(Continued)

*Primary Examiner* — Fekadeselassie Girma
(74) *Attorney, Agent, or Firm* — Knobbe, Martens, Olson & Bear, LLP

(57) ABSTRACT

A method of patient management including receiving therapy data associated with a plurality of durable medical devices and a first set of patients, and displaying an overview of patient compliance and a plurality of customizable tiles. The overview of patient compliance includes at least the number of patients in the first set of patients, current compliance data, compliance history data, and follow-up data. The plurality of aligned tiles includes at least a title and a plurality of selectable subtitles, each of the plurality of selected subtitles associated with one or more rules. Upon selection of a first selectable subtitle, displaying at least an indication of patients in a second set of patients, wherein the second set of patients is a subset of the first set of patients;
(Continued)

upon selection of a first patient, displaying at least all of the rules triggered by the first patient.

18 Claims, 9 Drawing Sheets

Related U.S. Application Data

(60) Provisional application No. 62/450,819, filed on Jan. 26, 2017.

(51) Int. Cl.
    *G16H 40/67*     (2018.01)
    *G16H 50/30*     (2018.01)
    *A61B 5/00*     (2006.01)
    *A61M 16/00*     (2006.01)

(52) U.S. Cl.
    CPC ........ *A61M 16/0051* (2013.01); *G16H 20/40* (2018.01); *G16H 40/67* (2018.01); *G16H 50/30* (2018.01); *A61M 2205/3584* (2013.01); *A61M 2205/502* (2013.01)

(56) References Cited

U.S. PATENT DOCUMENTS

| | | | | |
|---|---|---|---|---|
| 2008/0114689 | A1* | 5/2008 | Psynik | H04L 63/0272 705/51 |
| 2010/0292544 | A1* | 11/2010 | Sherman | A61B 5/00 128/204.23 |
| 2011/0073107 | A1* | 3/2011 | Rodman | G16H 40/63 141/2 |
| 2013/0297350 | A1* | 11/2013 | Gross | G16H 40/63 705/3 |
| 2014/0032231 | A1* | 1/2014 | Semen | G16H 40/63 705/2 |
| 2014/0150791 | A1* | 6/2014 | Birnkrant | G16H 20/40 128/204.23 |
| 2017/0216541 | A1* | 8/2017 | Truschel | A61M 16/0069 |
| 2017/0232214 | A1* | 8/2017 | Walsh | A61M 16/021 128/202.22 |
| 2018/0236191 | A1* | 8/2018 | Martin | A61M 16/026 |
| 2018/0286510 | A1* | 10/2018 | Kwan | G06Q 10/20 |
| 2020/0090485 | A1 | 3/2020 | Casse et al. | |
| 2020/0246566 | A1* | 8/2020 | Sherman | A61B 5/08 |
| 2020/0261673 | A1* | 8/2020 | Hickey | H04W 12/50 |
| 2022/0172595 | A1* | 6/2022 | Casse | G08B 21/0453 |

FOREIGN PATENT DOCUMENTS

| | | |
|---|---|---|
| WO | WO 2015/179915 | 12/2015 |
| WO | WO 2015/179916 | 12/2015 |
| WO | WO 2016/019292 | 2/2016 |
| WO | WO 2016/022974 | 2/2016 |

OTHER PUBLICATIONS

Extended European Search Report for 18744482.3 dated Oct. 30, 2020 in 7 pages.

\* cited by examiner

FIG. 5B

| NAME | STATUS | COMPLIANCE | COMPLIANCE RATE | AVG USAGE | PHONE NO. | ACTIONS | MANAGE |
|---|---|---|---|---|---|---|---|
| ☒ Bill Spady | NEW | | | | (732) 914-8509 | ℞ 📧 ✉ | DISMISS ALL |
| REVIEW<br>Patient At risk of non compliance after 7 days<br>Efficiency Above 40 lpm for more than 7 days<br>Efficiency Above 30 AHI for more than 14 days | | | AHI<br>34/h | Mask-Sinplus<br>82.4 lpm | | Sleep hours<br>09:59 | Patient profile → |
| ③ Chi Sanzone | NEW | Compliant | 86% | 4.0 hrs | (826) 500-7625 | ℞ 📧 ✉ | Select ⌄ |
| ② Alesha Holland | NEW | Compliant | 85% | 7.2 hrs | (571) 122-4818 | ℞ 📧 ✉ | Select ⌄ |
| Christian Hum | NEW | Compliant | 95% | 3.7 hrs | (212) 628-0030 | ℞ 📧 ✉ | Select ⌄ |
| Latonya Starcher | FOLLOW UP | Compliant | 89% | 5.0 hrs | (771) 591-2823 | ℞ 📧 ✉ | Select ⌄ |
| Olevia Cruse | FOLLOW UP | Compliant | 94% | 6.3 hrs | (694) 807-5768 | ℞ 📧 ✉ | Select ⌄ |
| Karine Avery | NEW | Compliant | 100% | 8.3 hrs | (775) 879-6270 | ℞ 📧 ✉ | Select ⌄ |

At risk of non-compliance: 10
At risk of non-compliance within 7 days
Non compliant / Compliant
Compliant 30 - 90 days: 9
At risk of non-compliance within 7 days
Patient follow up
New patient follow up after 2 Days: 10

500B, 566, 568, 569a, 569b, 569c

Efficacy

| Mask Leak | | AHI | | Treatment hours | | 8 ✕ |
|---|---|---|---|---|---|---|

Efficacy: Mask leak above 40 lpm for more than 7 days ⟵ 662

| NAME | STATUS | MASK LEAK | SLEEP HOURS | AHI | PHONE NO. | ACTIONS | MANAGE |
|---|---|---|---|---|---|---|---|
| [3] Sylvester Gattison | NEW | 29.4 lpm | 07:18 | 24 /h | (826) 500-7625 | ℞ 🗓 ▷ | Select ⌄ |
| [2] Kyle Folks | NEW | 29.2 lpm | 03:41 | 51 /h | (571) 122-4818 | ℞ 🗓 ▷ | Select ⌄ |
| [2] Nannette Rosner | NEW | 25.1 lpm | 01:58 | 41 /h | (212) 628-0030 | ℞ 🗓 ▷ | Select ⌄ |
| Dorthea Costilla | NEW | 16.6 lpm | 08:28 | 37 /h | (771) 591-2823 | ℞ 🗓 ▷ | Select ⌄ |
| Krystina Donovan | FOLLOW UP | 51.6 lpm | 00:24 | 98 /h | (694) 807-5768 | ℞ 🗓 ▷ | Select ⌄ |
| Verda Thakkar | FOLLOW UP | 51.6 lpm | 08:54 | 81 /h | (228) 687-2587 | ℞ 🗓 ▷ | Select ⌄ |
| Jem Tennison | NEW | 29.4 lpm | 06:42 | 76 /h | (582) 491-5498 | ℞ 🗓 ▷ | Select ⌄ |
| Hanh Pratts | FOLLOW UP | 82.5 lpm | 04:47 | 3 /h | (495) 543-4870 | ℞ 🗓 ▷ | Select ⌄ |

| Efficacy | | | | | | |
|---|---|---|---|---|---|---|
| Mask Leak | | | AHI | | Treatment hours | |

Efficacy: Mask leak above 40 lpm for more than 7 days     8   X

| NAME | STATUS | MASK LEAK | SLEEP HOURS | AHI | PHONE NO. | ACTIONS | MANAGE |
|---|---|---|---|---|---|---|---|
| ③ Sylvester Gattison | NEW | 29.4 lpm | 07:18 | 24/h | (826) 500-7625 | ☒ 🗐 ✉ | Select ▼ |

674 — Select ▼ : Exclude / Contacted / Unable to Contact

676 — Sylvester Gattison row

FIG. 6B

Patient note ✕

History gonor action turpes noroque. Nec Cars turpes penanous prom on vem placerat porta diam, pulvinar ac

Appered in Rule | 02:32 pm
Sleep Hours for less than 4 Hours for more than 30 days
28 August 2016

Appered in Rule | 04:12 pm
AHI Above 40 AHI for more than 7 days
↳ Dismissed for 7 days on 21 August 2016

Phoned patient to follow up | 12:30 am
12 June 2016

Add new note

SAVE NOTE

METHOD AND SYSTEM FOR PATIENT MANAGEMENT USING RULES ENGINE

INCORPORATION BY REFERENCE TO ANY PRIORITY APPLICATIONS

This application is a continuation of U.S. patent application Ser. No. 16/481,047, filed Mar. 6, 2020, which is a U.S. National Phase of International Patent Application No. PCT/IB2018/050472, filed Jan. 26, 2018, which claims priority to U.S. Provisional Application No. 62/450,819, filed Jan. 26, 2017, which is hereby incorporated by reference herein in its entirety.

Any and all applications for which a foreign or domestic priority claim is identified in the Application Data Sheet as filed with the present application are hereby incorporated by reference under 37 CFR 1.57.

FIELD OF THE INVENTION

The present technology is directed towards management of therapy for the amelioration, treatment, or prevention of respiratory disorders. More specifically, it is directed towards a patient management system having a rules engine to monitor patient compliance.

BACKGROUND TO THE INVENTION

Insurance companies, or other reimbursing entities (payors), often require evidence that a patient prescribed with respiratory pressure therapy has been compliant, that is, used their respiratory pressure therapy ("RPT") device according to certain a compliance standard before reimbursing the patient for the RPT device. Compliance standards generally require some minimum amount of usage per session for some fraction of a number of consecutive sessions known as the compliance period. One example of a compliance standard for Continuous Positive Airway Pressure (CPAP) therapy common to many payors, known as the CMS compliance standard, is that a patient is required to use the RPT device for at least four hours a night on at least 21 of 30 consecutive days. In order to determine a patient's compliance, a provider of the RPT device (such as a durable medical equipment provider or DME agent, also sometimes referred to as a home medical equipment provider or HME agent) may manually obtain data describing the patient's therapy using the RPT device, calculate the device usage from the therapy data, and compare the usage with the compliance standard. Once the DME agent has determined that the patient is compliant according to the compliance standard, the DME agent may notify the reimbursing entity that the patient is compliant. This process can be costly, time-consuming, and error-prone if conducted manually. RPT devices typically therefore contain data management capability that enables the RPT device to store and transmit therapy data to a remote server to determine automatically whether the patient has used the RPT device in accordance with the compliance standard.

SUMMARY OF THE INVENTION

In a first aspect there is provided a patient management system comprising:
a data management server in communication with a plurality of durable medical equipment (DME) devices configured to provide a therapy to a plurality of patients, the data management server configured to:
receive, via a network, data from each of the plurality of DME devices, wherein the data comprises at least one of DME therapy data or patient identifying data,
assess the received data, and
based at least in part on a determination that the received data satisfies at least one rule, cause an indication of an alert condition.

The plurality of DME devices may comprise a plurality of respiratory pressure therapy devices.

Each of the plurality of respiratory pressure therapy devices may be configured to deliver respiratory pressure therapy to a patient in the form of pressurized air to an airway of the patient during a therapy session.

The data may comprise one or more variables of therapy delivered to the patient by at least one of the plurality of DME devices.

The data management server may be further configured to:
identify an action of a plurality of actions;
perform the identified action;
adjust one or more settings of the alert condition, wherein said adjusting includes at least muting the alert condition; and
re-assess the received data.

The identified action may comprise at least one of add patient notes, update prescription data, contact a patient, order new equipment, or generate a patient report.

Said updating prescription data may comprise at least one of modifying, cancelling, or renewing a prescription.

To assess the received data, the patient management system may be configured to determine patient compliance based at least in part on a monitored therapy treatment of the one or more patients and a prescribed therapy treatment of the one or more patients.

Said muting the alert condition may comprise muting the alert condition for a predefined period of time.

The rule may comprise a condition associated with at least one of patient usage data, therapy duration, timestamp information or equipment information.

Each rule of the plurality of rules may define a set of patients that satisfies a particular rule, wherein a set of patients that satisfies the particular rule is a subset of the plurality of patients of which therapy is provided by the plurality of DME devices.

The data management server may be further configured to cause a display to display information indicative of one or more of the plurality of rules and information indicative of one or more patients.

Satisfying a rule may indicate that a patient is not in compliance with a prescribed therapy treatment.

The data management server may be further configured to cause an indication that one or more patients do not meet one or more efficacy thresholds.

In another aspect there is provided a method of patient management comprising:
assessing activity of one or more patients of a group of patients;
indicating an alert condition is present based at least in part on the assessed activity, the alert condition indicative of one or more patients satisfying one or more rules;
receiving a first action of a plurality of actions;
performing the first received action;
adjusting one or more settings of the alert condition, wherein said adjusting includes at least muting the alert condition; and
re-assessing patient activity.

Each action of the plurality of actions may be associated with at least one of adding patient notes, updating prescription data, contacting one or more patients, ordering new equipment, and generating a patient report.

Updating prescription data may comprise at least one of modifying, cancelling, or renewing a prescription.

Said assessing activity may comprise determining patient compliance based at least in part on a monitored therapy treatment of the one or more patients and a prescribed therapy treatment of the one or more patients.

Muting the alert condition may comprise muting the alert condition for a predefined period of time.

The one or more rules may include a condition associated with at least one of patient usage data, therapy duration, timestamp information, equipment information.

Each rule of the one or more rules may define a set of patients that satisfies the associated rule, wherein the set of patients that satisfies the associated rule is a subset of the group of patients of which activity is assessed.

The method may further comprise displaying information indicative of one or more of the plurality of rules and information indicative of one or more patients.

Satisfaction by a first patient of one or more rules may indicate that the first patient is not in compliance with a prescribed therapy treatment.

The method may further comprise providing indication that one or more patients do not meet one or more efficacy thresholds.

In another aspect there is provided a patient management system comprising:
 a data management server in communication with a plurality of DME devices and configured to receive use data from the plurality of DME devices, wherein the use data is associated with a first set of the plurality of patients; and
 a patient compliance monitoring system in communication with the data management server, wherein the patient compliance monitoring system is configured to provide a displayed indication of the use data for the plurality of DMEs, wherein the displayed indication of the use data comprises:
  an overview of patient compliance, wherein the overview of patient compliance includes at least a number of patients in the first set of patients, current compliance data, compliance history data, and follow-up data; and
  a plurality of customizable tiles, wherein the plurality of customizable tiles includes at least a title and a plurality of selectable subtitles, each of the plurality of selected subtitles associated with one or more rules;
 wherein the patient compliance monitoring system is further configured to:
  receive a first selection of a first selectable subtitle;
  responsive to the selection of a first selectable subtitle, update the displayed indication to include an indication of one or more patients in a second set of patients, wherein the second set of patients is a subset of the first set of patients;
  receive a second selection corresponding to a first patient of the second set of patients, and responsive to the second selection, update the displayed indication to include an indication of one or more rules triggered by the first patient.

The one or more rules may be associated with at least one of patient usage data, therapy duration, timestamp information, equipment information.

The display device may be further configured to provide an indication that one or more patients do not meet one or more efficacy thresholds.

The one or more efficacy thresholds may be variable efficacy thresholds.

The one or more variable efficacy thresholds may comprise one or more moving averages.

The one or more rules triggered by the first patient may indicate that the first patient is at risk of non-compliance with a prescribed therapy treatment.

The displayed indication may further include a report, the report comprising information associated with at least one of monitored patient performance, patient notes, proscribed patient treatment, and patient identifying information.

In another aspect there is provided a method of patient management comprising:
 receiving therapy data associated with a plurality of durable medical devices and a first set of patients;
 causing a display to display an overview of patient compliance and a plurality of customizable tiles, wherein the overview of patient compliance includes at least the number of patients in the first set of patients, current compliance data, compliance history data, and follow-up data, wherein the plurality of customizable tiles include at least a title and a plurality of selectable subtitles, each of the plurality of selected subtitles associated with one or more rules;
 responsive to a selection of a first selectable subtitle, causing the display to display at least an indication of one or more patients in a second set of patients, wherein the second set of patients is a subset of the first set of patients; and
 responsive to a selection of a first patient, causing the display to display at least one or more rules triggered by the first patient.

The one or more rules may be associated with at least one of patient usage data, therapy duration, timestamp information, equipment information.

The method may further comprise providing indication that one or more patients do not meet one or more efficacy thresholds.

The one or more efficacy thresholds may be variable efficacy thresholds.

The one or more variable efficacy thresholds may comprise one or more moving averages.

The rule triggered may suggest that a patient is at risk of non-compliance with a prescribed therapy treatment.

The method may further comprise generating a report, the report comprising information associated with at least one of monitored patient performance, patient notes, proscribed patient treatment, and patient identifying information.

In another aspect there is provided a system which monitors patient compliance for a plurality of patients of prescriptions for using a plurality of durable medical devices (DMEs) in order to improve patient usage of the DMEs, the system comprising:
 a data management server in communication with the plurality of DMEs, the data management server configured to receive use information of the plurality of DMEs;
 a patient compliance monitoring system configured to provide a displayed indication of the use information of the plurality of DMEs, wherein the patient compliance monitoring system automatically organizes the use information based on one or more compliance rules preprogramed or selected by a user, the one or more compliance rules configured to organize the information into a format that indicates to a user information regarding compliance of the DMEs so that the user can determine one or more groupings of the plurality of patients that have similar compliance of the DMEs in order to allow the user to improve or confirm compliance with the prescriptions.

The displayed indication of the use information may comprise a plurality of tiles representing the one or more groupings of the plurality of patients that have similar compliance of the DMEs.

At least one tile of the plurality of tiles may represent patients of the plurality of patients at risk of non-compliance.

The at least one tile may represent patients at risk of non-compliance within 7 days, 14 days, or one month.

Each tile of the plurality of tiles may display a number of patients represented by the particular tile.

Each tile of the plurality of tiles may be configured to expand to list individual patient information.

Individual patient information may comprise at least a patient name and/or contact information.

Clicking on or selecting the patient name, the contact information, or other information of the individual patient information may automatically send a text or initiates a phone call.

The text or phone call may initiate an automated message to a patient identified by the individual patient information.

Clicking on or selecting the patient name, the contact information, or other information of the individual patient information may allow a user to can change the patient's prescription.

The automated message may comprise an indication of one or more links to tutorials to instruct the patient identified by the individual patient information as to how to improve that patient's usage and/or compliance.

The individual patient information may comprise an indication of previous contact attempts and/or results.

The individual patient information may comprise a compliance history.

The individual patient information may comprise an indication of recommended actions to improve patient compliance.

At least one tile of the plurality of tiles may comprise an indication of recommended actions to improve patient compliance.

At least one tile of the plurality of tiles may include metrics for patients of a particular group of the plurality of patients.

The individual patient information may comprise Apnea-Hypopnea Index (AHI) information.

The individual patient information may comprise an indication of an amount of time a particular patient uses a DME of the plurality of DMEs.

At least one tile of the plurality of tiles may represent patients of the plurality of patients which are non-compliant.

The at least one tile may represent patients which have been non-compliant for at least 30 days or at least 90 days.

At least one tile of the plurality of tiles may represent patients of the plurality of patients to follow up with.

The at least one tile may represent patients to follow up with after 2 days, 1 week, or 2 weeks.

In another aspect there is provided a method for monitoring patient compliance for a plurality of patients of prescriptions for using a plurality of durable medical devices (DMEs) in order to improve patient usage of the DMEs, the method comprising:

receiving, at a data management server in communication with the plurality of DMEs, use information of the plurality of DMEs;

providing, via a patient compliance monitoring system, a displayed indication of the use information of the plurality of DMEs; and automatically organizing the use information based on one or more compliance rules preprogramed or selected by a user, the one or more compliance rules configured to organize the information into a format that indicates to the user information regarding compliance of the DMEs so that the user can determine one or more groupings of the plurality of patients that have similar compliance of the DMEs in order to allow the user to improve or confirm compliance with the prescriptions.

The displayed indication of the use information may comprise a plurality of tiles representing the one or more groupings of the plurality of patients that have similar compliance of the DMEs.

At least one tile of the plurality of tiles may represent patients of the plurality of patients at risk of non-compliance.

The at least one tile may represent patients at risk of non-compliance within 7 days, 14 days, or one month.

Each tile of the plurality of tiles may display a number of patients represented by the particular tile.

The method may further comprise responsive to a selection of a first tile of the plurality of tiles, causing the displayed indication of the use information to display an expanded list of individual patient information.

Individual patient information may comprise at least a patient name and/or contact information.

The method may further comprise automatically sending a text or initiating a phone call in response to a user clicking on or selecting the patient name, the contact information, or other information of the individual patient information.

The text or phone call may initiate an automated message to a patient identified by the individual patient information.

The automated message may comprise an indication of one or more links to tutorials to instruct the patient identified by the individual patient information as to how to improve that patient's usage and/or compliance.

The method may further comprise changing the patient's prescription in response to a user clicking on or selecting the patient name, the contact information, or other information of the individual patient information.

The individual patient information may comprise an indication of previous contact attempts and/or results.

The individual patient information may comprise a compliance history.

The individual patient information may comprise an indication of recommended actions to improve patient compliance.

At least one tile of the plurality of tiles may comprise an indication of recommended actions to improve patient compliance.

At least one tile of the plurality of tiles may comprise metrics for patients of a particular group of the plurality of patients.

The individual patient information may comprise Apnea-Hypopnea Index (AHI) information The individual patient information may comprise an indication of an amount of time a particular patient uses a DME of the plurality of DMEs.

At least one tile of the plurality of tiles may represent patients of the plurality of patients which are non-compliant.

The at least one tile may represent patients which have been non-compliant for at least 30 days or at least 90 days.

At least one tile of the plurality of tiles may represent patients of the plurality of patients to follow up with.

The at least one tile may represent patients to follow up with after 2 days, 1 week, or 2 weeks.

For purposes of summarizing the disclosure, certain aspects, advantages and novel features of several embodiments have been described herein. It is to be understood that not necessarily all such advantages can be achieved in accordance with any particular embodiment of the embodiments disclosed herein. Thus, the embodiments disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

FIG. 5B illustrates an example display responsive to a selection of a patient name.

FIG. 6A illustrates an example display responsive to a selection of a subtitle.

FIG. 6B illustrates actions available to the DME agent, according to some embodiments.

FIG. 7 illustrates recorded patient notes within the patient management system, according to some embodiments.

DETAILED DESCRIPTION

Figure 1:
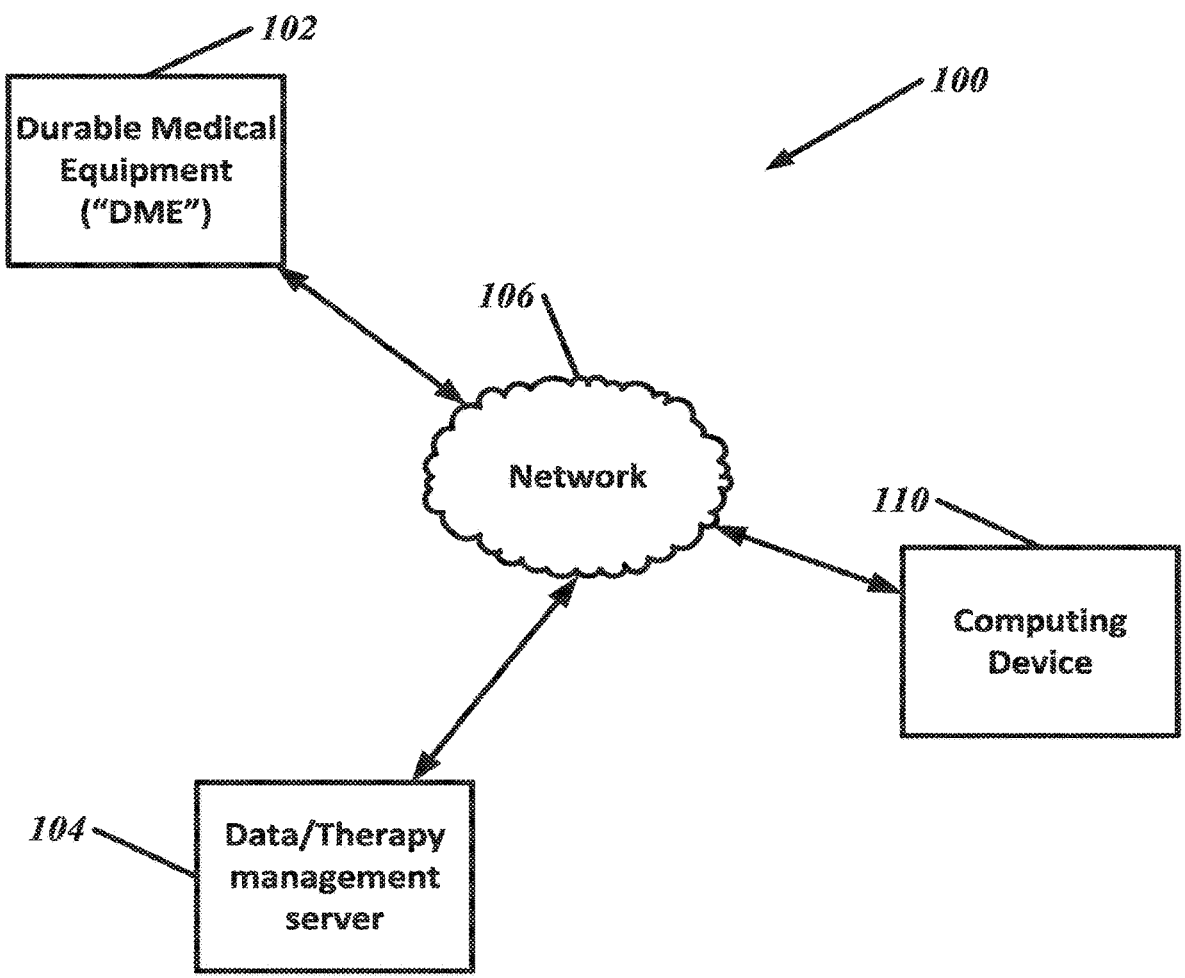
FIG. 1 is a block diagram of a patient management system according to some embodiments.

Studies have shown that many of patients prescribed with CPAP therapy, non-invasive ventilation therapy, nasal high flow therapy, and the like have at least some problems meeting compliance standards. While strict underperformance thresholds are widely used to provide an alert to a DME agent, the strict thresholds have proven unhelpful due to constant underperformance alerts. Accordingly, a need exists to provide a DME agent with a simple user interface to manage patients, track compliance, and provide a notification when actions need to be taken with respect to individual patients. In addition, a need exists to monitor one or more rolling averages rather than absolute thresholds. For example, implementing variable efficacy thresholds allows incremental improvement of a user's performance over time without providing constant underperformance alerts.

Additionally, the strong need exists to further improve patient outcomes, raise the compliance rate of patients, and decrease the rate of non-compliance related insurance coverage issues. In addition, there exists a need to provide DME agents with information about the progress of their patients' therapy, in such a way that patients experiencing compliance difficulties are prominently featured. For instance, the patient management system can provide a history of patient usage and DME agent actions. In addition, the patient management system can provide warnings that indicate that a patient is as risk of non-compliance if that patient continues therapy at her current actual usage.

The disclosed patient management system applies a number of rules to data obtained from one or more medical devices to monitor patient compliance and allow users to be grouped according to their characteristics, as defined by the rules. Each rule can include a condition that is related to one of more features of any combination of patient usage data, therapy duration, timestamp information, equipment information, and other external data. A rule is satisfied if the characteristics of the input data to the rule satisfy the specified characteristics of the rule. The rules can include a variety of conditions, ranging from time-based conditions to compliance risk conditions.

The patient management system can apply one or more rules or rule sets to data obtained from a medical device associated with a patient. Each rule defines a group of patients that satisfy the rule. After patients are grouped according to appropriate rule sets, the rules and members of each group are displayed for the DME agent, healthcare professional or service provider on the patient management system graphical user interface (GUI). The rules can be used to determine which patients are not in compliance (or are below an optical compliance) with the prescribed therapy treatment. Accordingly, "satisfying" or "triggering" a rule may be an indication that the patient is in non-compliance with a prescribed therapy treatment, an indication that sub-optimal therapy has been recognized, or an indication that some other event of interest to a DME agent's therapy management (or administrative processes) has been identified.

For purposes of this disclosure and as non-limiting examples, a DME agent can be a distributor of durable medical equipment, an intermediary between an insurance company (or payor) and a patient, or someone who is otherwise allied with the insurance company (or payor) such as a contractor.

To facilitate patient compliance monitoring, a standard set of rules is provided within the patient management system. Additionally, if a DME agent wants a rule outside the standard rule set, he or she can compose a new rule or make a request that a new rule be written. For example, the rules may be written in a script editor or composed using a graphical "drag and drop" interface having predetermined blocks. Creating new rules can be especially advantageous when a DME agent is concerned with more than one clinical parameter. For example, a DME agent may desire a rule providing an alert for a high (Apnea-Hypopnea Index) AHI and a corresponding high mask leak.

The standard set of rules and/or the rules displayed on the patient management system GUI can vary from country to country. For example, the United States has specific compliance criteria that relates to a provider's ability to obtain reimbursement from an insurer. In this market, rulesets that specifically identify patients at risk of non-payment would be included. In Australia, it is important that a patient can quickly acclimatize to a medical device (for example, a CPAP) and achieve and articulable benefit. Thus, in this market, rules focused on ensuring patients are getting a full night's sleep (for example, 6 or more hours) while using their device without technical issues (such as high mask leak) would be included.

The variety of payors and/or insurance companies may also have an effect on the standard set of rules and/or the rules displayed on the patient management system GUI. This is because different payors and/or insurance companies may have differing rules regarding the requirements of their customers for being compliant. For example, a first insurance company may require 70% compliance at a minimum of 4 hours per night over a 30 day period, while a second insurance company may also require a specific AHI threshold. In this example, a different set of rules may be used for the first insurance company and the second insurance company. Thus, the same rules are not necessarily applied or displayed uniformly to all patients whose data are in the patient management system.

In some examples, the parameters relevant to the patient's insurance company and/or payor can be entered manually by a DME agent. The patient management system can save the conditions for compliance of a newly entered insurance company such that the same conditions can be applied to a subsequently entered patient covered by the same insurance company. In other examples, the patient management system is packaged to include a number of common insurance company compliance parameters, and the DME agent can select the relevant insurance company from a list.

Adjustable Efficacy Thresholds

Many parameters, such as efficacy thresholds, can be monitored by applying the rules as disclosed herein. Efficacy thresholds relevant to OSA treatment, for example the Apnea-Hypopnea Index (AHI), mask leak, occurrences of central apneas, changes in sleep hours, changes in sleep patterns (for instance, what times a patient is sleeping and waking), changes in environmental conditions, and changes in subjective data (such as mood collected from supporting Apps), are thresholds that measure the ability of the therapy to produce a desired or intended result. These efficacy thresholds can be useful in providing insight into the effectiveness of respiratory therapy at treating a patient suffering from OSA.

Different or supplemental thresholds can be monitored by applying the rules as herein disclosed for different respiratory therapy treatments. For example, for nasal high flow treatment, device usage duration, patient respiratory rate and patient blood oxygen levels or blood oxygen saturation are thresholds that can provide an indication of treatment effectiveness, and can provide a measure of the ability of the therapy to produce a desired or intended result.

The data used to determine the threshold values can be measured and recorded by the durable medical equipment during treatment. Treatment sessions may be a number of times per day, for example once per day. This treatment frequency is usually expected for OSA respiratory therapy if the patient has one primary sleep block or session per day, or nasal high flow treatment prescriptions with a single treatment session per day. Treatment sessions may occur multiple times per day, as would be the case for OSA treatment with more than one sleep block per day, or nasal high flow treatment prescriptions with multiple treatment sessions per day. For example, a nasal high flow treatment prescription can include five treatment sessions, each lasting one hour, within a twenty four hour period.

The standard set of rules and/or the rules displayed on the patient management system GUI can also vary from disease to disease, or disease state to disease state. For example, a patient suffering from OSA will have different compliance criteria, and different relevant compliance metrics to a patient suffering from Chronic Obstructive Pulmonary Disease (COPD). Thus, for OSA patients, rules relating to AHI, mask leak, or other parameters can be included in the standard set of rules, while for COPD patients, rules relating to device usage duration, respiratory rate and blood oxygen levels can be included.

As one example of an efficacy threshold, the AHI is an index used to indicate the severity of sleep apnea. It is represented by the number of apnea and hypopnea events per hour of sleep. Combining AHI and oxygen desaturation gives an overall sleep apnea severity score that evaluates both the number of sleep disruptions and the degree of oxygen desaturation. The AHI is calculated by dividing the number of apnea events by the number of hours of sleep. The AHI values for adults are categorized as: Normal (0-4); Mild sleep apnea (5-14); Moderate sleep apnea (15-29); and Severe sleep apnea (30+).

Typically, patient management systems have fixed AHI thresholds that, when not satisfied, provide an alert indicating underperformance. For instance, if a patient's AHI is above 5, an alert may be provided to the DME agent to indicate the therapy isn't working at a sufficient level.

Advantageously, in addition to fixed efficacy thresholds, the rules of the disclosed patient management system also utilize adjustable efficacy thresholds (for example, for floating or time-dependent thresholds). Accordingly, as opposed to a rule that applies equally to all patients (for example, a rule which notifies the DME agent if a patient has an AHI above a fixed threshold of 5), the described patient management system can include a rule that alerts to the DME agent based on patient improvements and/or a comparison of moving averages.

For example, a patient having an AHI of 10 would generally trigger a rule of AHI>5. However, if that patient had an AHI of 30 prior to undertaking respiratory pressure therapy, it may be advantageous not to trigger an alert to the DME agent because the patient is most-likely experiencing a significant improvement in sleep quality. Thus, although the patient would generally trigger a rule of AHI>5 which would alert the DME agent, in some examples, the rule is not triggered because of patient's improvement.

In addition, one or more moving or rolling averages may be utilized to determine whether a DME agent should be alerted. In the context of the AHI, a moving average of the user's AHI can be calculated over a relatively longer time frame ($AHI_{long}$) such as a 30 day period and a relatively shorter time frame ($AHI_{short}$) such as a 5 day period. In some embodiments, $AHI_{long}$ can be 14, 21, 30, or 60 days (+/− few days). In some embodiments, $AHI_{short}$ can be 1, 2, 3, 4, 5, 8, 10, or 14 days (+/− few days).

Accordingly, the system can monitor any deviation of $AHI_{short}$ from $AHI_{long}$. If $AHI_{short}$ (for example, an AHI of 10) is less than $AHI_{long}$ (for example, an AHI of 30), then the patient's sleep is improving and the system can advantageously decline to send an alarm to the DME agent, although the patient would trigger a rule of AHI>5. Moreover, if $AHI_{short}$ (for example, an AHI of 15) is greater than $AHI_{long}$ (for example, an AHI of 10), then the system can trigger an alarm in addition to the alarm for the rule of AHI>5 because the patient is getting worse. In some examples, if $AHI_{short}$ is greater than $AHI_{long}$, a notification can be provided to the DME agent indicating that a condition (for instance, possible high mask leak) is present that is detrimental to the effectiveness of the therapy on the user.

In some embodiments, the difference between the $AHI_{short}$ and $AHI_{long}$ must satisfy a specified percentage or a fixed value in order to suppress an alarm. For example, an alarm may be suppressed if the $AHI_{short}$ is 10 index points less than $AHI_{long}$. Similarly, in some embodiments, an alarm (or notification) can be provided to the DME agent when the $AHI_{short}$ is greater than $AHI_{long}$ by a fixed percentage or fixed value. For example, the $AHI_{short}$ may be low enough not to trigger an alarm for the rule of AHI>5. However, an alarm can still be triggered if that $AHI_{short}$ is five index points greater than $AHI_{long}$. In some examples, the fixed value is 2, 4, 6, 8, 10, 12, 14, or 16 index points (+/− a few index points). In some examples, the specified percentage is 5, 10, 15, 20, 25, 30, 40, or 50 percent (+/− a few percent).

Accordingly, as opposed to a rule that applies equally to all patients (for example, a rule which notifies the DME agent if a patient has an AHI above a fixed threshold of 5), the described patient management system can include a rule that alerts (or suppresses an alert to) the DME agent if the $AHI_{short}$ deviates from the $AHI_{long}$. For example, if $AHI_{long}$ is 10 and $AHI_{short}$ passes over 15, then an alarm for the rule of $AHI_{short}$>$AHI_{long}$ can be triggered.

Patient management system rules can include exceptions that prevent generation of alerts, or automatically mute or hide alerts in certain circumstances. The exceptions can, for example be implemented for large percentage changes of low nominal value thresholds or efficacy metrics. This is because a large percentage increase of a low nominal threshold value is also nominally smaller than the same percentage increase of an originally larger nominal threshold value. Although both percentage increases are the same, the end effect on the patient can be more significant or more noticeable for the larger nominal increase, and can go unnoticed, or be of smaller significance for the patient with the lower nominal increase.

For example, a central apnea rule can be included in the patient management system that provides an alert to the DME if greater than 30% of apneas detected relating to an OSA patient are determined to be central apneas. This rule can provide a useful indication into the effectiveness of the respiratory therapy, and a useful indication into how the treatment can be adjusted or supplemented to improve future performance. If the patient has a low nominal number of obstructive apneas and central apneas however, the rule can provide an alert when not necessary, or when said alert won't provide meaningful information to the DME about the patient's treatment. For example, an increase in central apneas per hour from 0 to 2 of the patient undergoing respiratory therapy and experiencing 2 obstructive apneas in the same time period, in percentage terms is a large increase, as now 50% of apneas are central. In practical terms however, such a small nominal change in central apneas is unlikely to significantly affect treatment or efficacy, and as such, an alert as a result of this change may not be of use. A central apnea rule exception can therefore mute, hide, or prevent from being generated alerts for the rule, if the nominal number of central apneas is below a nominal threshold, for example 5. The limit or nominal threshold at which the exception stops taking effect can be pre-included in the generic rule, or can be manually set or adjusted by the DME agent, healthcare professional or service provider.

The central apnea rule can therefore include an exception criteria that mutes, hides or prevents an alert being generated for large percentage increases in the number of central apneas, or ratio of central to obstructive apneas, where the nominal increase is low.

More generally, exceptions can be implemented in the rules of the patient management system to avoid generation of alerts, or automatically mute or hide the alerts in circumstances where no action is required, or where action would not materially benefit the patient. These exemptions can be tailored on a patient-by-patient basis, rule-by-rule basis or can be generic.

As mentioned above, similar patient based adjustable efficacy metrics can be applied to mask leak, occurrences of central apneas, changes in sleep hours, changes in sleep patterns (for instance, what times a patient is sleeping and waking), changes in environmental conditions, changes in subjective data (such as mood collected from supporting Apps), and the like.

FIG. 1 is a block diagram of a patient management system 100 according to some embodiments. The patient management system 100 includes durable medical equipment 102, a data/therapy management server 104, one or more computers 110, and a network 106. In some examples, the patient management system 100 can omit one or more of these elements. Similarly, the patient management system 100 can include additional elements. For example, in some instances the data/therapy management server 104 can include a data/therapy management server and a therapy management server.

The durable medical equipment 102 is configured to provide therapy to a patient, transmit data regarding therapy provided to the patient to the data/therapy management server 104 via the network 106, and/or monitor the patient. In some examples, the durable medical equipment 102 can include a single device or more than one device. For purposes of this disclosure, DME is any equipment that provides therapeutic benefits to a patient in need because of certain medical conditions and/or illnesses.

In some embodiments, the durable medical equipment 102 can include a respiratory pressure therapy ("RPT") device configured to deliver respiratory pressure therapy to the patient in the form of pressurized air to an airway of the patient during a therapy session. In some examples, the medical device is a continuous positive airway pressure (CPAP) device. In some examples, the therapy data collected and/or transmitted by the durable medical equipment 102 can include device settings and/or therapy data describing one or more variables of the therapy delivered to the patient. For example, the therapy data can include AHI, machine runtime, machine usage time, average pressure, 90th percentile pressure, max pressure reached, average leak, 90th percentile leak, time with excessive leak, apnea index, hypopnea index, central index, flow limitation index, humidity, awake state detections, duration of awake state on, ambient temperature, ambient humidity, pressure settings, comfort settings (for example, awake state and or expiratory relief settings), apnea events, hypopnea events, AHI, flow limitation events, ramps, central events, flow rate, treatment pressure, leak flow rate and the like. In some instances, one or more therapy data can be monitored and/or recorded at predefined intervals. For instance, the data can be monitored and/or recorded at 30 second, 1 minute, 2 minute, 5 minute, 10 minute, 15 minute, or 30 minutes intervals (+/− a few minutes). In some instances, one or more therapy data can be monitored and/or recorded at predefined frequencies. For example, flow rate, therapy pressure, and/or leak rate can be at monitored and/or recorded at 1-50 HZ. In some examples, the durable medical equipment 102 transmits data to the data/therapy management server 104, which can compute the one or more therapy data.

Also connected to the network 106 is a computing device 110 that is associated with an agent of the durable medical equipment 102 that is responsible for the therapy of the patient. As mentioned above, the DME agent can be a distributor of durable medical equipment, an intermediary between an insurance company (or payor) and a patient, or someone who is otherwise allied with the insurance company (or payor) such as a contractor. The agent can interact with the data/therapy management server 104 over the network 106 via a client program running on the computing device 110. The computing device 110 may be any desktop or portable (laptop or notebook) computer, tablet computer, PDA, netbook or smartphone, and the like.

The patient management system 100 can also contain a patient computing device (not shown), associated with a patient, connected to the network 106. The patient computing device can be a personal computer, mobile phone, tablet computer, or other device and can be configured to intermediate between the patient and the remotely located entities of the patient management system 100 (for example, the therapy management server 104), over the network 106. In some implementations, this intermediation is accomplished by a patient program that runs on the patient computing device. The patient program may be referred to as a "patient app".

In some examples, the durable medical equipment 102 is not connected to the network 106, but is configured to communicate with the patient computing device via a local wired or wireless network (not shown) based on a protocol such as Bluetooth or Wi-Fi. In this alternative implementation, the patient computing device (for example, via the patient app), intermediates between the durable medical equipment and the remotely located entities of the patient management system over the network 106.

The patient management system 100 can contain information on more than one patient, each patient with associated durable medical equipment and one or more DME agents. Each DME agent can be responsible for the therapy of one or more patients.

Figure 2:
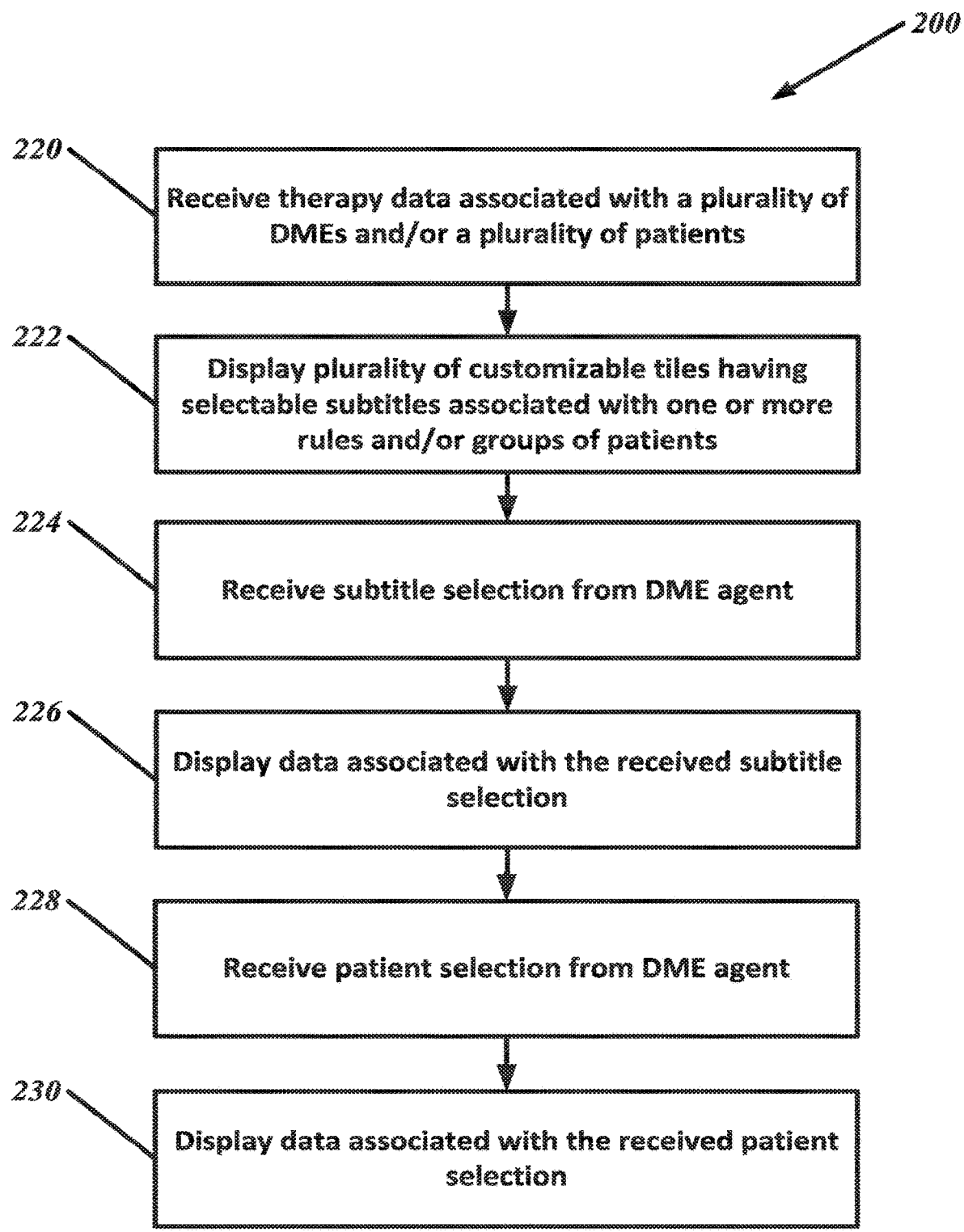
FIG. 2 is a flow chart illustrating a process carried out by the therapy management server 104 in the patient management system of FIG. 1, according to some embodiments.

FIG. 2 is a flow chart illustrating a process 200 carried out by the server 104 in the patient management system 100 of FIG. 1, according to some embodiments. The method 200 may be carried out each time the server 104 receives data from the durable medical equipment 102 or on a regular schedule such as every 8, 12, 24, 36, 48, or 72 hours.

At block 220, the sever 104 receives data associated with a plurality of durable medical equipment. As mentioned above, this data can include AHI, machine runtime, machine usage time, average pressure, 90th percentile pressure, max pressure reached, average leak, 90th percentile leak, time with excessive leak, apnea index, hypopnea index, central index, flow limitation index, humidity, awake state detections, duration of awake state, ambient temperature, ambient humidity, pressure settings, comfort settings (for example, awake state and/or expiratory relief settings), apnea events, hypopnea events, Apnea/Hypopnea Index (AHI), flow limitation events, ramps, central events, flow rate, treatment pressure, leak flow rate and the like.

At block 222, the patient management system GUI displays a plurality of customizable tiles. As described in more detail with respect to FIG. 4, each tile includes a title and one or more selectable subtitles. Each subtitle represents a group of patients which satisfies an associated rule. A DME agent can interface with the GUI, for example, to review patient compliance information related to one of more features of any combination of patient usage data, time, equipment information, and other external data. In some examples, the GUI is displayed after a successful login to the therapy management server program.

At block 224, the DME agent selects one of the selectable subtitles from the GUI. The subtitles can be selected by clicking a pointing device of the computing device on the subtitle text.

At block 226, the GUI displays data associated with the subtitle selection. As described in more detail with respect to FIG. 5A, the display shows the rule title and the number of patients whose data is complicity with the defined rule. Each patient within the associated group is listed, along with key metrics or context specific data, including context dependent data points extracted from the patient's complete data set. Displaying context specific data can help the DME agent or the viewer of the patient data to quickly establish a possible root cause for issues the patient may be having, and act to rectify them.

At block 228, the DME agent makes a patient selection. The patient selection can be made by clicking a pointing device of the computing device on the patient text. Alternatively, the display can include a selectable icon which, when selected, will cause the display to show all the rules that have been triggered by the selected patient.

At block 230, the GUI displays data associated with the patient selection. As described in more detail with respect to FIG. 5B, the display shows all the rules relevant to the selected patient as well as other patient data, for instance, AHI, Mask data and Sleep Hours.

Figure 3:
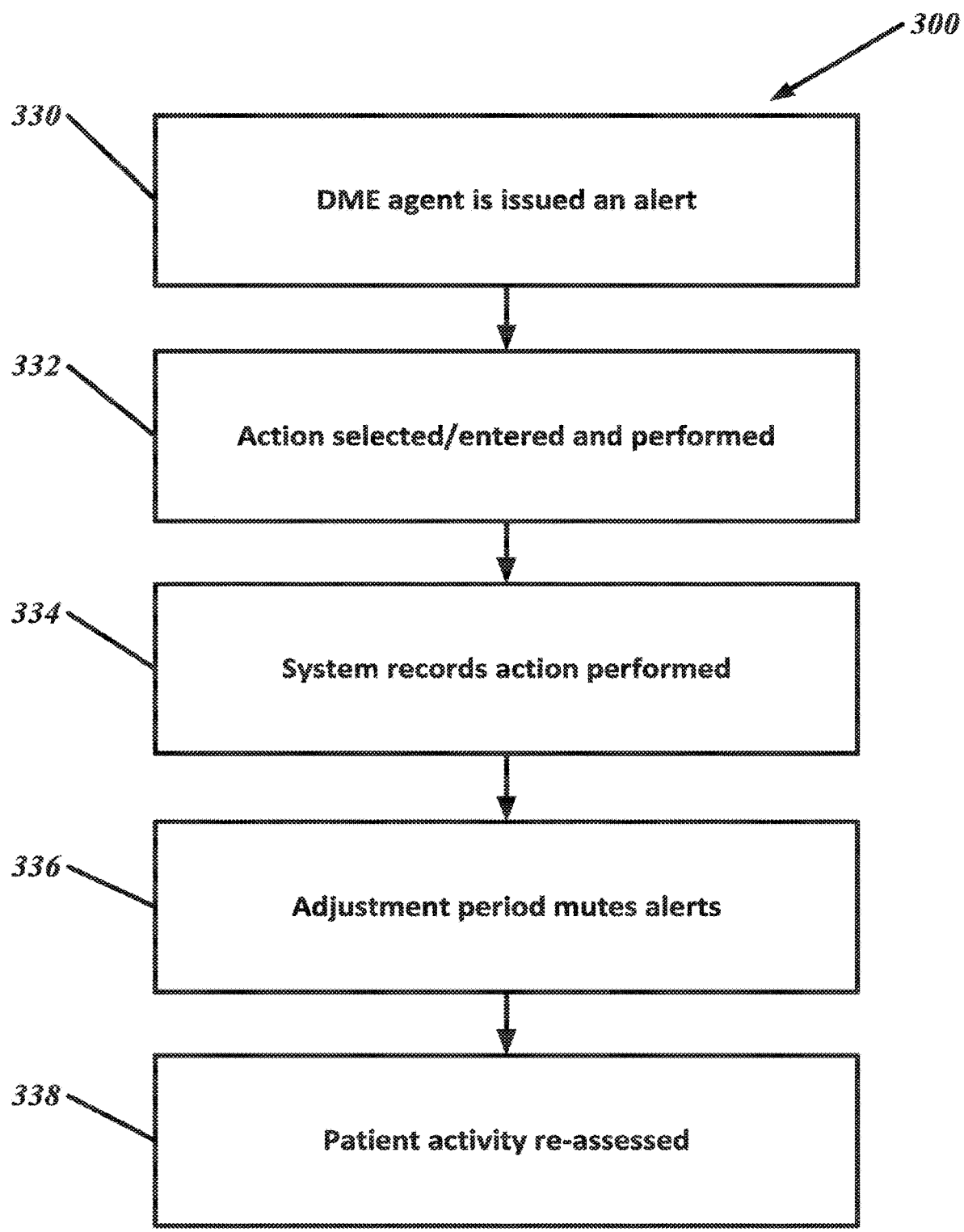
FIG. 3 is a flow chart illustrating a process carried out by the therapy management server 104 in the patient management system of FIG. 1, according to some embodiments

FIG. 3 is a flow chart illustrating a process 200 of the patient management system, according to some embodiments. At block 330, patient management system issues an alert to a DME agent which notifies the DME agent that a patient triggered at least one of the rules.

At block 332, an action is selected, entered and performed. FIG. 6B illustrates a variety of options available to the DME agent after an alert or notification is issued. These options allow the DME agent to add or remove a patient from a rule and/or temporarily dismiss a rule. As depicted in FIG. 6B, the DME agent has an option to mark the patient as "Contacted," "Unable to Contact" and "Exclude."

In some examples, the patient management system can predict a set of likely DME agent actions for a particular condition and/or alert. If the DME agent wishes to pursue one of the predicted options, the DME agent can select it from a list and enter the relevant parameters (for example, new operating pressure). In some examples, a list of predicted actions can actively prioritize (for example, rank according to effectivity) based on the success of previous occurrences when the same action has been performed on patients with similar characteristics. Logistic regression models or similar machine learning approaches can be used to train algorithms to classify like patients and assess action effectivity.

At block 334, the system records the action selected by the DME agent. As described below, each patient in the system has a set of notes that contain relevant patient information. The notes can be updated manually by the DME agent using an add note field and can also be updated or added to automatically. Advantageously, notes can be automatically recorded upon the occurrence of certain events. For instance, rule exceptions, overdue data, prescription changes, changes to the patient's therapy, rules that the patient is isolated into based on his usage data, and any other significant activity that happen in the system can be automatically noted in the patient's records.

At block 336, in response to an action by the DME agent, the system can temporarily withhold or dismiss the patient from that associated rule to afford the action time to have an effect. This is beneficial when an action has been taken that will take a certain amount of time to affect the patient's usage data. For example, if a new mask is ordered to replace an old, leaking mask, it could take 1-2 weeks before the patient receives his new mask. Therefore, the patient can be temporarily dismissed from the rule for a time period (the "settling period") in order to provide the patient a reasonable time to receive the shipment, setup the new equipment, and/or change a behavior that is causing the alert. For example, because behavior change can take time, the settling period can allow a patient time to settle in and make changes to his behavior without causing false positive alerts which could be ultimately fixed by the changed behavior.

At block 338, after the settling period has expired, the patient can be reassessed as to whether the action has been effective in resolving the patient's issue. If the patient's issue has been fixed, then the patient will no longer trigger the rule. If the patient's issue has not been fixed by the action, the patient's status can be changed from NEW to FOLLOW UP.

Figure 4:
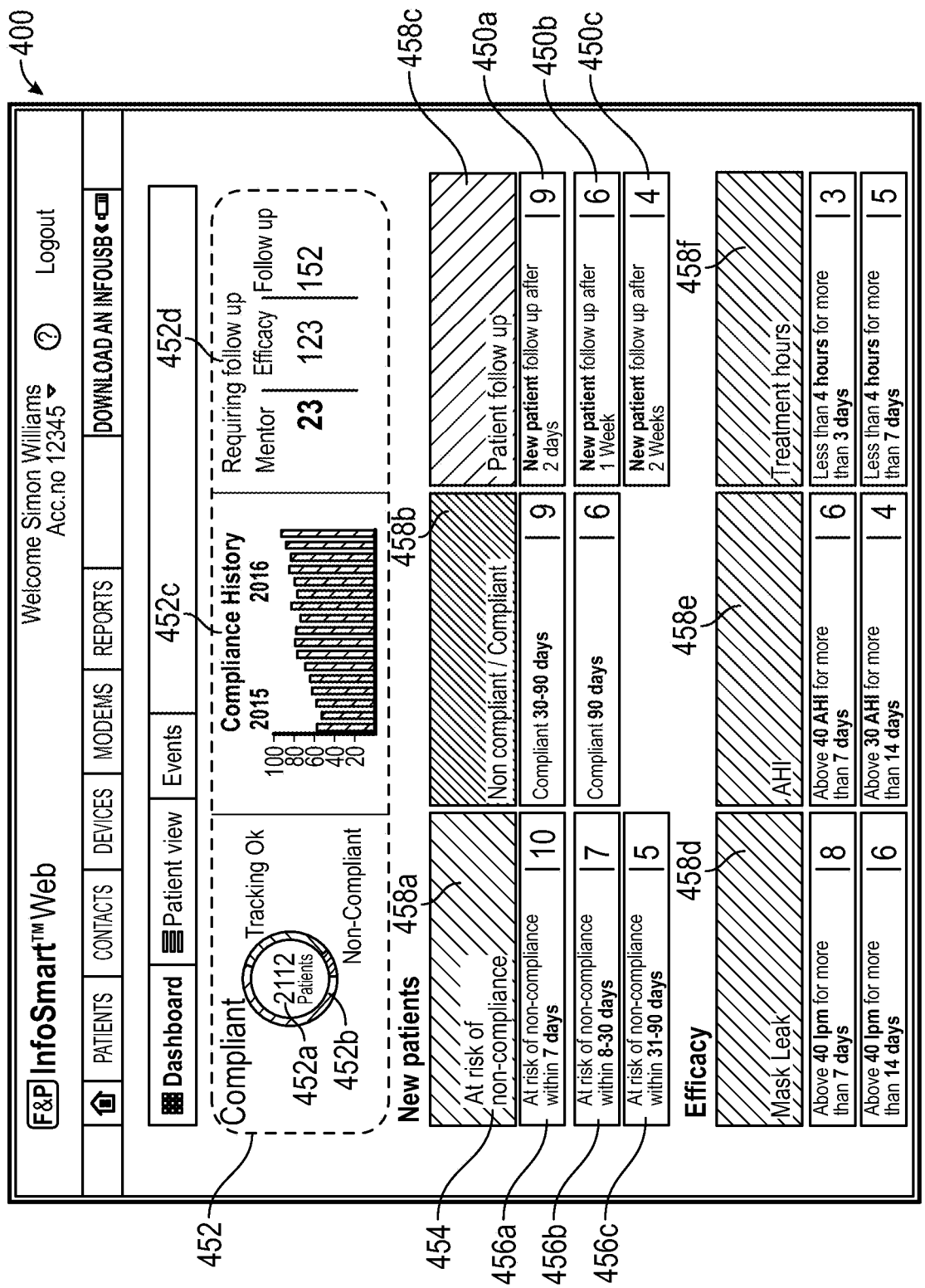
FIG. 4 illustrates a graphical user interface ("GUI") presented on a display according to some embodiments.

FIG. 4 illustrates a graphical user interface ("GUI") 400 presented on a display having a plurality of customizable tiles 458a-458f (collectively 458), according to some embodiments. As mentioned above, a DME agent (or appropriate individual) can interface with the GUI 400, for example, to review patient compliance information related to one or more features of any combination of patient usage data, time, equipment information, and other external data. In some examples, the GUI 400 is displayed after a successful login to the therapy management server program.

As depicted in FIG. 4, the GUI 400 includes a plurality of customizable tiles 458 positioned beneath an overview of patient compliance 452. In alternate embodiments, the tiles 458 and the overview of patient compliance data 452 can be located in altered positions. For example, the tiles 458 can be positioned at the top of the GUI 400 and/or around the overview of patient compliance data 452.

Each tile 458 includes a title (for example, "At risk of non-compliance" 454) and one or more subtitles (for example, "At risk of non-compliance within 7 days" 456a, "At risk of non-compliance within 8-30 days" 456b, and "At risk of non-compliance within 31-90 days" 456c). In some examples, the title is representative of the collective set of subtitles within the particular tile. For instance, "At risk of non-compliance" 454 collectively describes subtitles 456a, 456b, and 456c (collectively 456).

Each subtitle (for example, subtitle 456a) represents a group of patient(s) which satisfies an associated rule. In some examples, the subtitles can be selected (for example, by clicking a pointing device of the computing device 270 on the subtitle text) so as to cause the display to display data corresponding to the group of patients associated with the selected subtitle. As described in more detail with respect to FIG. 5, responsive to a subtitle selection, the display can display an indication of a patient (such as a patient's name) and/or therapy data of the patients in the associated group. In some, a patient's name may not be available and/or appropriate to display. For example, the Health Insurance Portability and Accountability Act (HIPPA) may restrict use of a patient name. In such instances, other indications of a patient can be displayed such as an identification number associated with the patient and the like.

The text of a subtitle can summarize the rule and/or group associated with that subtitle. For instance, the subtitle, "Compliant 30-90 days" in tile 458b can represent a group containing all of the patients which have been compliant for 30 to 90 days.

A specific selectable rule within a tile 458 can be dependent, independent or interdependent on the one or more other selectable rule within the associated tile. As an example, two rules may overlap and yield at least one of the same patients. In some instances, an individual patient which satisfies two or more rules will be presented in only one of the rules (for example, the "more urgent" rule). For example, if a patient triggers both, "at risk of non-compliance within 7 days" and "at risk of compliance within 14 days," the patient may only be displayed in the 7 day rule because the patient necessarily triggers the 14 day rule. As a result, the rules can be interdependently linked so that if a particular patient is shown in the 7 day rule, that particular patient is not shown in the 14 day rule. For example, if a patient triggers both, "at risk of non-compliance within 7 days" and "at risk of non-compliance within 14 days," the patient may only be displayed in the 7 day rule. However, it will be understood that, in some embodiments, an individual patient can be displayed in each of the rules he or she satisfies.

In some examples, the number of patients in a group (for example, the number of patients satisfying the associated rule) is also displayed within each tile 458 (for example, 450a, 450b, and 450c.)

The GUI can also present on the display an overview of patient compliance 452. In some examples, such as illustrated in FIG. 4, the overview of patient compliance 452 can include the number of monitored patients 452a, current compliance data 452b, compliance history 452b, and data regarding patients requiring a follow-up 452d. In alternative examples, the GUI 400 presents the overview of patient compliance 452 to the DME agent in a manner that emphasizes where potential problems lie and thus where attention is most needed. As described above with respect to adjustable efficacy thresholds, potential problems can be determined based on variable thresholds.

Figure 5A:
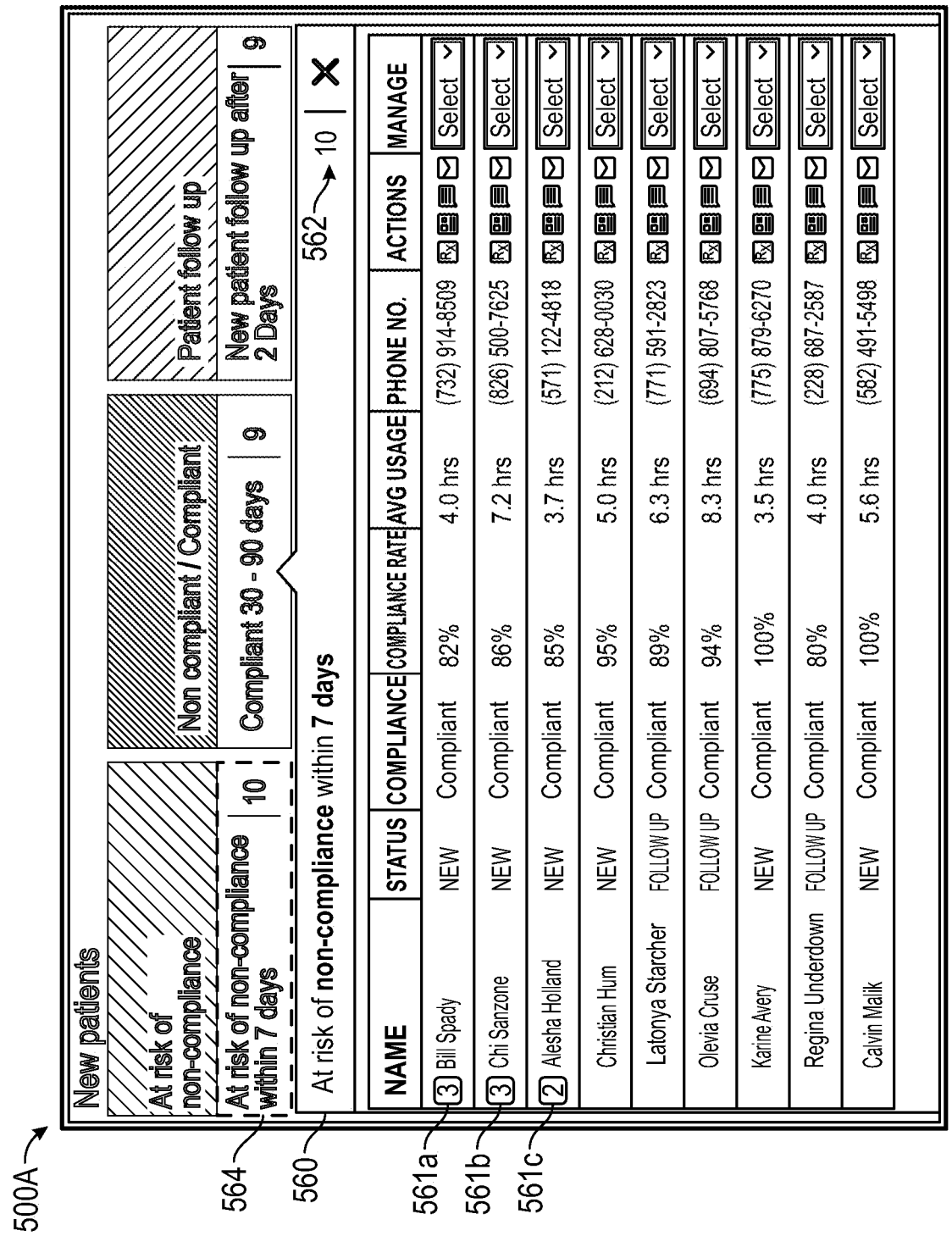
FIG. 5A illustrates an example display responsive to a selection of a subtitle.

FIG. 5A illustrates a display 500A responsive to a selection of the "At risk of non-compliance within 7 days" subtitle of FIG. 4, according to some embodiments. As mentioned above, the plurality of subtitles of FIG. 4 are each associated with a rule and a group of patients conforming to the rule. In this example, the display 500A shows the rule title (such as the selected subtitle) and the number of patients whose data is complicity with the defined rule. Each patient within the associated group is listed, along with key metrics or context specific data, including context dependent data points extracted from the patient's complete data set. Displaying context specific data can help the DME agent or the viewer of the patient data to quickly establish a possible root cause for issues the patient may be having, and act to rectify them.

The display can include for each patient of the group of patients, a patient name, patient status (for example, new or follow-up patient), compliance status (for example, compliant or non-compliant), compliance rate (for example, since the beginning of their treatment or over the past 30 days), average use (for example, the average number of hours the patient has used the therapy during the past 7 days), and patient phone number. Additionally, as described in more detail with respect to FIGS. 6A and 6B, the display can include a plurality of selectable actions associated with each patient.

In this example, a set of patients are displayed which conform to the requirements of a rule specifying they are at risk of non-compliance within 7 days. From the display 500A, a user (for example, a DME agent) can select a patient name. The patient name can be selectable (as described above with respect to the subtitles of FIG. 4) or, alternatively, the display can include a selectable icon 561a, 561b, and 561c (collectively 561). In either example, upon selecting a selectable patient name or a selectable icon 561, the display will show all the rules triggered by the selected patient (as shown in FIG. 5B).

The selectable icons 561 can indicate the number of rules relevant to a specific patient. For example, selectable icon 561a indicates that three rules are relevant to the associated patient. In some instances, as depicted in FIG. 5A, patients associated with only a single rule may not have a selectable icon associated with their name because all relevant rules are already being displayed.

FIG. 5B displays all of the rules applicable to the selected patient 566 according to some embodiments. In this example, the selected patient 566 triggers two other rules in addition to the non-compliance after 7 days rule. By displaying all of the rules associated with a selected patient, a DME agent can more easily keep track of patient performance.

In the illustrated example, all the rules 568 relevant to the selected patient 566 are shown as well as other patient data 569a, 569b, and 569c (collectively 569). Although FIG. 5B depicts the displayed patient data as AHI 569a, Mask data 569b, and Sleep Hours 569c, any of the aforementioned therapy data can be displayed.

FIG. 6A illustrates a display 600A responsive to a selection of the "Mask leak above 40 lpm for more than 7 days" subtitle of FIG. 4, according to some embodiments. As mentioned above, the plurality of subtitles of FIG. 4 are each associated with a rule and a group of patients conforming to the rule. In this example, the display 600A shows the rule title and the number of patients whose data is complicity with the defined mask leak rule. Each patient within the associated group is listed, along with key metrics or context specific data.

The context specific data 662 shown for this rule includes the average mask leak per night for the past 7 nights (liters per minute), sleep hours and each patient's Apnea-Hypopnea Index (AHI). The parameters that are shown for each rule are configurable, for instance, by a DME agent. As a result, if the DME agent finds easy access to a particular set of parameters beneficial in treating patients, and the set is different from the standard parameters, the DME agent can change to the preferred parameters.

FIG. 6A also illustrates a variety of actions 664, 668, 670, 672 that are available to the DME agent. After selecting a patient from a list, the DME agent can perform a number of activities which may help diagnose or address a problem further. These include viewing a report of the patient's performance 668, changing the patient's prescription 664, adding notes 670, or emailing the patient 672.

The change prescription action 664 allows a DME agent to change, cancel or renew a patient prescription based on, for instance, the displayed data. In some examples, the DME agent can modify the prescription if it is determined that the pressure or humidity delivered to the patient is too high or too low. In some examples, when a prescription is changed, cancelled or renewed, the user's device can be updated (for instance, automatically updated) with the new prescription information. Responsive to the alteration of the prescription, the user can get a notification indicating the change and/or instructions on how the user should proceed with his or her treatment.

As described further with respect to FIG. 7, the patient note action 670 allows a DME agent to manually add notes on the patient that can be saved and utilized to generate historical records. In addition, notes can be automatically recorded upon the occurrence of certain events. For instance, rule exceptions, overdue data, prescription changes, changes to the patient's therapy, rules that the patient has triggered based on his usage data, and any other significant activity that happen in the system can be automatically noted in the patient's records. Thus, the notes provide an effective route to track a patient's therapy timeline.

The viewing a report action 668 generates a report on the patient's therapy usage and efficacy for display. By viewing this report, a DME agent can review a timeline of notes, rules, etc. The DME agent can use the report to determine historical rule triggers, review activities taken in the past such as prescription changes, and see any prior patient notes.

The email patient action 672 allows the DME agent to email the patient, for instance, to inform him about his treatment. As an example, the DME agent may desire to email the patient about a high leak over the past 7 days and propose a solution such as tightening the headgear or getting a new mask. In some examples, the patient management system can alternatively or additionally allow the DME agent to text or automatically call (for instance, via automated message) the patient's phone. Alternatively, where the patient has an app installed on his smartphone, the system can send a notification to the app for delivery to the patient. More details regarding courses of action after a DME agent is notified or alerted are described below.

In some embodiments, in order to avoid potential Health Insurance Portability and Accountability Act (HIPAA) issues, the email patient action 672 is not available. In examples such as these, the DME agent is still able to provide guidance and/or direction to the patient. For instance, the patient monitoring system can include an option allowing the DME agent to select from a smart filtered list of possible support material to send to the patient. For example, if the triggered rule is related to mask leak, these smart-filtered options could be links that show videos or PDF guides on mask fitting, tightening, and/or cleaning for the patient.

FIG. 6B illustrates a variety of options available to the DME agent after an alert or notification is issued. These options allow the DME agent to add or remove a patient from a rule and/or temporarily dismiss a rule. As depicted in FIG. 6B, the DME agent has an option to mark the patient as "Contacted," "Unable to Contact" and "Exclude."

Following a notification, the DME agent can perform an action relevant to the alert. The patient management system can record the action in the patient's notes, store data relating to the action, and adjust a patient's alert thresholds or required actions for the future. In some examples, the patient management system can predict a set of likely DME agent actions for a particular condition and/or alert. If the DME agent wishes to pursue one of the predicted options, the DME agent can select it from a list and enter the relevant parameters (for example, new operating pressure). In some examples, a list of predicted actions can actively prioritize (for example, rank according to effectivity) based on the success of previous occurrences when the same action has been performed on patients with similar characteristics. Logistic regression models or similar machine learning approaches can be used to train algorithms to classify like patients and assess action effectivity.

A patient is marked as "contacted" if an action has been performed (for instance, by a DME agent) that may resolve an issue relevant to the alert and ultimately remove the patient from the rule. For example, if a patient has ordered new equipment to replace leaky or broken equipment, the DME agent can mark the patient as contacted because the new equipment may resolve the patient's issues.

In response to a patient being identified as "contacted" with respect to a specific rule, the system temporarily withholds or dismisses the patient from that associated rule to afford the action time to have an effect. This is beneficial when an action has been taken that will take a certain amount of time to affect the patient's usage data. For example, if a new mask is ordered to replace an old, leaking mask, it could take 1-2 weeks before the patient receives his new mask. Therefore, the patient can be temporarily dismissed from the rule for a time period (the "settling period") in order to provide the patient a reasonable time to receive the shipment and setup the new equipment. For instance, the settling period can be 3 days, 1 week, 2 weeks, 3 weeks etc. In some instances, the settling period is predefined by the system. In other examples, the settling period may be chosen, for instance, by the DME agent. This approach can drastically reduce the amount of "false positives" (for example, alerts based on issued that will soon be resolved) providers have to deal with.

After the settling period has expired, the patient can be reassessed as to whether the action has been effective in resolving the patient's issue, thereby removing the patient from the rule. If the patient's issue has not been fixed by the action, the patient's status 676 can be changed from NEW to FOLLOW UP.

As another example, the DME agent or physician may decide to adjust the prescription of a patient where the patient is detected to have high AHI, even with treatment. Following the action of adjusting the prescription, the patient management system can automatically mute high AHI alerts for the settling period (for example, 7 days), during which time the user is able to adjust to the new therapy parameters. The patients performance is then be reassessed at the end of the settling period, and if their behavior is still applicable with the rule, the DME is alerted again.

The settling period can also be implemented in the rule sets utilizing moving averages, as described above. For example, after a patient with a high mask leak has his mask replaced, he is likely to have a lower mask leak. Over time, the short term moving average of mask leak and long term moving average of mask leak should reduce to reflect this. As a result, muting the mask leak alarm for the settling period will allow for a re-adjustment of the moving averages that are used as a base line metric for measuring the patient's mask leak.

A patient is marked as "unable to contact" in the event that the DME agent attempted to contact the patient to implement a change in therapy or to provide information as required but the patient was unreachable. In some examples, the patient management system can automatically record in the patient's notes that the DME agent attempted to contact the patient however they were unavailable. The patient management system can also record the time at which the patient was attempted to be contacted and/or the methods attempted. In other examples, the DME agent can manually update the notes.

In some examples, upon being identified as "unable to contact," the system temporarily (for example, 1 or 2 days) withholds or dismisses the patient from that associated rule. This advantageously provides time for the DME agent to find another way to contact the patient and/or time for the patient to remedy his own situation. Additionally, by temporarily removing the patient from the rule, it provides the DME agent assess to patients which still need attention for the day. After the short temporary period (for example, 12 hours, 1 day, 2, days, etc.) expires, the patient is automatically added back to the rule to provide the DME agent another opportunity to remedy the patient's issue. The patient is returned to the list without the status of NEW, allowing a subsequent attempt to contact the patient and resolve the issue to be made.

A patient is marked as "exclude" when the DME agent decides to remove the patient from the rule, although the patient is not strictly adhering to the rule as applied to all patients. Utilizing this feature, the alerts can advantageously be muted if the DME agent has attempted to rectify the situation multiple times to no avail, or the patient is not contactable. This option can also be utilized to mute the alerts where it is determined that the patient is performing acceptably, even in the case where an alert may be being indicated as they aren't meeting a certain desired threshold. For instance, the DME agent may desire to exclude the patient from the rule if the patient is benefiting from the therapy in a noticeable way, although not strictly adhering to a rule applied to all patients. For example, if the patient's AHI is 10 but is experiencing improved sleep quality, he can be removed from an AHI>5 rule that may typically applied to all patients, even though they don't strictly meet the typical threshold.

FIG. 7 illustrates recorded patient notes within the patient management system, according to some embodiments. As described above, each patient in the system has a set of notes that contain relevant patient information. The notes can be updated manually by the DME agent using the add note field 784 and can also be updated or added to automatically.

Advantageously, notes can be automatically recorded upon the occurrence of certain events. For instance, rule exceptions, overdue data, prescription changes, changes to the patient's therapy, rules that the patient is isolated into based on his usage data 782, and any other significant activity that happen in the system can be automatically noted in the patient's records. Thus, the notes provide an effective route to track a patient's therapy timeline 780, generate historical records, review a history of past conditions and past attempted remedies, and determine recurring conditions.

In some examples, the patient management system can automatically record in the patient's notes that the DME agent attempted to contact the patient however they were unavailable. The patient management system can also record the time at which the patient was attempted to be contacted and/or the methods attempted. In other examples, the DME agent can manually update the notes.

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, methods, etc. described herein. A wide variety of variation is possible. Components, elements, and/or steps can be altered, added, removed, or rearranged. While certain embodiments have been explicitly described, other embodiments will become apparent to those of ordinary skill in the art based on this disclosure.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A patient management system comprising:
    a data management server in communication with a plurality of durable medical equipment (DME) devices and configured to receive use data from the plurality of DME devices, wherein the use data is associated with a first set of patients; and
    a patient compliance monitoring system in communication with the data management server, wherein the patient compliance monitoring system is configured to provide a displayed indication of the use data for the plurality of DME devices, wherein the displayed indication of the use data comprises:
        an overview of patient compliance, wherein the overview of patient compliance includes at least a number of patients in the first set of patients, current compliance data, compliance history data, or follow-up data; and
        a plurality of customizable tiles, wherein the plurality of customizable tiles include at least a title and a plurality of selectable subtitles, each of the plurality of selected subtitles associated with one or more rules;
    wherein the patient compliance monitoring system is further configured to:
        receive a first selection of a first selectable subtitle of the plurality of selectable subtitles;
        responsive to the selection of the first selectable subtitle, update the displayed indication to include an indication of one or more patients in a second set of patients, wherein the second set of patients is a subset of the first set of patients;
        receive a second selection corresponding to a first patient of the second set of patients, and
        responsive to the second selection, update the displayed indication to include an indication of one or more rules triggered by the first patient.

2. The patient management system of claim 1, wherein the plurality of DME devices comprise nasal high flow (NHF) devices.

3. The patient management system of claim 1, wherein the plurality of DME devices comprise Continuous Positive Airway Pressure (CPAP) devices.

4. The patient management system of claim 1, wherein the one or more rules are associated with at least one of patient usage data, therapy duration, timestamp information, or equipment information.

5. The patient management system of claim 1, wherein the display device is further configured to provide an indication that one or more patients do not meet one or more efficacy thresholds.

6. The patient management system of claim 5, wherein the one or more efficacy thresholds are variable efficacy thresholds.

7. The patient management system of claim 6, wherein the one or more variable efficacy thresholds comprise one or more moving averages.

8. The patient management system of claim 1, wherein the one or more rules triggered by the first patient indicate that the first patient is at risk of non-compliance with a prescribed therapy treatment.

9. The patient management system of claim 1, wherein the displayed indication further includes a report, the report comprising information associated with at least one of monitored patient performance, patient notes, proscribed patient treatment, or patient identifying information.

10. A method of patient management comprising:
    receiving therapy data associated with a plurality of durable medical equipment (DME) devices and a first set of patients;
    causing a display to display an overview of patient compliance and a plurality of customizable tiles, wherein the overview of patient compliance includes at least a number of patients in the first set of patients, current compliance data, compliance history data, and follow-up data, wherein the plurality of customizable tiles include at least a title and a plurality of selectable subtitles, each of the plurality of selected subtitles associated with one or more rules;
    responsive to a selection of a first selectable subtitle of the plurality of selectable subtitles, causing the display to display at least an indication of one or more patients in a second set of patients, wherein the second set of patients is a subset of the first set of patients; and
    responsive to a selection of a first patient of the second set of patients, causing the display to display at least one or more rules triggered by the first patient.

11. The method of claim 10, wherein the plurality of DME devices comprise nasal high flow (NHF) devices.

12. The method of claim 10, wherein the plurality of DME devices comprise Continuous Positive Airway Pressure (CPAP) devices.

13. The method of claim 10, wherein the one or more rules are associated with at least one of patient usage data, therapy duration, timestamp information, or equipment information.

14. The method of claim 10, further comprising providing an indication that one or more patients do not meet one or more efficacy thresholds.

15. The method of claim 14, wherein the one or more efficacy thresholds are variable efficacy thresholds.

16. The method of claim 15, wherein the one or more variable efficacy thresholds comprise one or more moving averages.

17. The method of claim 10, wherein the at least one or more rules triggered suggest that a patient is at risk of non-compliance with a prescribed therapy treatment.

18. The method of claim 10, further comprising generating a report, the report comprising information associated with at least one of monitored patient performance, patient notes, proscribed patient treatment, or patient identifying information.

* * * * *